United States Patent [19]
Jochimsen

[11] Patent Number: 4,876,069
[45] Date of Patent: Oct. 24, 1989

[54] BLOOD CLOTTING TIME MEASURING APPARATUS

[76] Inventor: Siegfried Jochimsen, Falckstrasse 19, DE-2300, Kiel, Fed. Rep. of Germany

[21] Appl. No.: 924,155

[22] Filed: Oct. 27, 1986

Related U.S. Application Data

[63] Continuation of Ser. No. 483,950, Mar. 8, 1983, abandoned.

[30] Foreign Application Priority Data

Jul. 11, 1981 [DE] Fed. Rep. of Germany ....... 3127560
Nov. 19, 1981 [DE] Fed. Rep. of Germany ....... 3145692

[51] Int. Cl.⁴ ..................... G01N 21/59; G01N 33/86
[52] U.S. Cl. ......................... 422/73; 73/64.1;
356/39; 356/442; 366/273; 366/274; 436/69
[58] Field of Search .............. 436/69; 435/13; 422/73;
73/64.1; 356/39, 442; 366/273, 274

[56] References Cited

U.S. PATENT DOCUMENTS

| 2,516,965 | 8/1950 | Dresser | 422/104 X |
| 3,488,156 | 1/1970 | Good et al. | 422/73 |
| 3,550,619 | 12/1970 | Halasz et al. | 422/104 X |
| 3,593,568 | 7/1971 | Schmitz et al. | 73/64.1 |
| 3,595,531 | 7/1971 | Williams et al. | |
| 3,833,864 | 9/1974 | Kiess et al. | 436/69 X |
| 3,905,482 | 9/1975 | Knulst | 422/104 X |
| 3,905,769 | 9/1975 | Carroll et al. | 356/39 X |
| 3,914,773 | 10/1975 | Harrower | 346/121 |
| 3,967,934 | 7/1976 | Seitz et al. | 422/73 |
| 4,007,013 | 2/1977 | Kotacka | 422/104 |
| 4,081,242 | 3/1978 | Girolami | 422/73 X |
| 4,135,818 | 1/1979 | Kent et al. | 356/39 |

FOREIGN PATENT DOCUMENTS 2039035 7/1980 United Kingdom .

OTHER PUBLICATIONS

Cambosco Order Book No. 200, Cambosco Scientific Co., Inc., Boston, Mass., 1965, p. 20.

Primary Examiner—Robert J. Hill, Jr.
Attorney, Agent, or Firm—Andrus, Sceales, Starke & Sawall

[57] ABSTRACT

Blood clotting time measuring apparatus has a temperature controlled cabinet with at least one measuring channel for receiving a measuring cell (17) containing a blood sample, the clotting time of which is to be measured. The cabinet includes clamping means (18) for retaining the measuring cell in said measuring channel. A magnetic stirrer (16, 16a) is mounted in the cabinet proximate to the measuring channel and has a metal ball (23) positionable in the measuring cell and magnetically operable with the stirrer. A photo optical turbidity detector has a light source (15) and a light detector (14) forming a photo optical path (32) containing the measuring cell. The light source receives an operating voltage which is at least half the rated voltage of said source. The light detector is connected to a measured value means (27) having two threshold value limiting means. In the measuring process, the sensing thresholds are established in accordance with the signal derived from the photo optical path prior to clotting to improve the accuracy of clotting time measurement.

12 Claims, 7 Drawing Sheets

BLOOD CLOTTING TIME MEASURING APPARATUS

CROSS REFERENCE TO RELATED APPLICATIONS

The present application is a continuation application of U.S. patent application Ser. No. 06/483,950, filed Mar. 8, 1983 and now abandoned.

The invention relates to a blood clotting time measuring apparatus and to a method for determining and measuring the blood clotting time. The technique of the present invention utilizes a temperature controllable metal unit receiving a measuring cell, a stirrer and a photooptical turbidity measuring device.

Various methods and apparatuses are already known for the purpose of determining and measuring the blood clotting time, which is dependent on the blood factors present in the blood. According to the Schnittger Gross small hooks method, small hooks are moved against one another during the measurement. When blood clotting takes place, there is conductivity change, which is measured and results in the automatic switching off of the apparatus. Apparatuses functioning according to this method can be used both for plasma and for whole blood, but do not permit an automatic start. In addition, the hooks can break and bend, whilst incorrect times can result from contamination.

It is also known to determine the blood clotting time by measuring the viscosity which changes during clotting. In an apparatus operating according to this method, a small plastic plate oscillates with a constant frequency in the plasma. A frequency shift occurs when clotting takes place and brings about a disconnection of the apparatus. It is advantageous that the apparatus can be used for both plasma and whole blood and also permits an automatic start. However, the sensitivity of the apparatus to vibrations and the fact that the apparatus is too insensitive in the pathological field represent disadvantages.

In the most frequently used apparatuses, the blood clotting time is determined by measuring the turbidity of the sample which occurs during blood clotting, it being conventional practice to use photooptical systems with a constant lamp voltage and a photoamplifier with a disconnection logic. These apparatuses permit an automatic start, prevent contamination and also have no movable parts. However, it is disadvantageous that due to the slight turbidity change occurring during clotting, a high amplification must be obtained. This high amplification necessarily leads to various interfering influences, e.g. a high sensitivity to extraneous light. Measurements with kaolin-stabilized reagents are not possible, because the kaolin settles during the measurement and this sedimentation leads to the switching off of the apparatus. Measurements with an oxalated plasma are also impossible, because intermediate turbidity actions occur, which also lead to premature disconnection. In addition, such apparatuses are very sensitive to vibrations. In order to be able to process different turbid reagents or plasmas by means of apparatuses with photooptical systems, it is necessary to use reversing switches, which enable the resetting of the amplification. Frequently, such apparatuses cannot be used if the reagents or plasma are too turbid, because the optimum operating point of the light absorber can no longer be reached through the excessively strongly darkened light path. In addition, the sensitivity of the apparatuses in the pathological range only generally extends up to approximately 25% Quick.

In order to obviate these disadvantages of the photooptical systems, it has already been proposed to additionally introduce a magnetic mixing system and an automatic lamp voltage control. The advantage of the magnetic measuring system is that at the start of clotting, the fibrin strands are activated and contract. This leads to a considerable turbidity change requiring no high amplification. Due to the constant mixing of the sample which persists during the measurement, the measurement is also made more uniform. However, such apparatuses also have disadvantages. Thus, in certain measuring methods, the mixing rod stresses the sample to such an extent that there can be considerable time lags. On adding the plasma to a measuring cell with a mixing rod, air occlusions frequently occur, because the rod forms a cavity on the cell wall. As the cavity is in the form of a rising air bubble, it can disturb the measuring process and lead to the disconnection of the apparatus. Due to the geometrically small shapes, it is difficult to separate the mixing rods, so that their uses requires a particular manual skill on the part of the person carrying out the measurement.

A lamp voltage control fundamentally has the advantage that the operating point of the photoabsorber remains relatively constant over a large turbidity range. Thus, generally no reversing switch is required for the sensitivity. However, it is a disadvantage of the known apparatuses that the operating voltage with clear reagents is generally approximately 20% of the rated voltage, which means that the light source is almost dark. Despite low amplification, the extraneous light influences are consequently very high, so that it is necessary to work with a light protection cap to avoid false measurements. As the amplification is the same with various turbid samples, incorrect measurements are easily possible in the case of clear reagents, because the difference in the turbidity change is not sufficient to switch off the apparatus. All known photooptical systems operate with a standard cell with a diameter of approximately 10 mm. On filling with 100 or 200 μl, there is also the serious disadvantage that the liquid level of many apparatuses is either in the lower or in the upper region of the light path. This prevents clearly defined optical values, so that self-starts can occur in the case of small liquid level fluctuations.

The object of the invention is to provide a blood clotting time measuring apparatus of the aforementioned type which, with easy handling of the measuring cells, allows a more reliable determination of the blood clotting time, without there being any risk of incorrect measurements due to uncontrolled turbulence in the sample or extraneous light entering through the cell opening. Another object of the invention is to construct the blood clotting time measuring apparatus in such a way that the clotting measuring curves can be optically represented.

According to the invention, this object is achieved by the combination of the following features:

(a) the stirrer is constructed in per se known manner as a magnetic stirrer located in the measuring block below the measuring channel used for receiving the measuring cells:

(b) the measuring cell contains as the stirring member a metal ball which can be brought into magnetic operative association with the magnetic stirrer;

(c) each measuring cell is held in the measuring channel by means of a clamping device;

(d) each measuring cell is in the photooptical path of a per se known photooptical scanner, whose light source receives an operating voltage, which is at least half as high as the rated voltage and whose light detector is connected to a measured value unit with two threshold value limiters.

BRIEF DESCRIPTION OF THE DRAWINGS

Further features of the invention are described in the specification and claims with respect to the apparatus represented in the drawings. The figures show:

Figure 1:
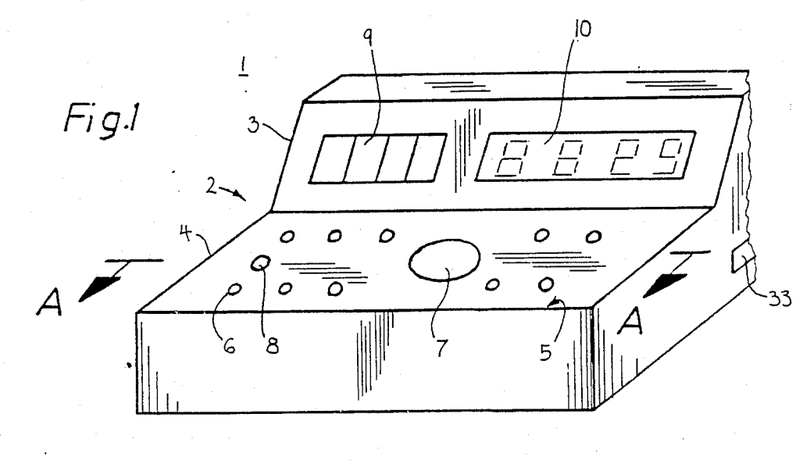
FIG. 1 an embodiment of the apparatus according to the invention in a perspective view.

FIG. 1 shows in perspective an apparatus 1 for determining and measuring the blood clotting time and has a control part 3 and a measuring part 4 combined in a casing 2. On control part 3 is constructed a control panel 9, which can for example have pushbutton or mercury switches. In addition, in the viewing plane of control part 3 is provided a display panel 10, which is preferably constructed as an alphanumeric display. In the measuring surface 5 of measuring part 4 there are provided several recesses, which lead into the temperature controllable measuring unit or block 11 (FIG. 2) made from metal or some other suitable material. These recesses serve as preheaters 6 for measuring cell 17 (FIG. 2) with plasma, as well as preheaters 7 for a glass with reagents. The measuring surface 5 also contains the measuring channel 8 for the particular measuring cell 17 to be investigated. For the power supply of apparatus 1, a connector 33 is provided, which permits a connection to power mains. Apparatus 1 can also be operated by a not shown battery.

Figure 2:
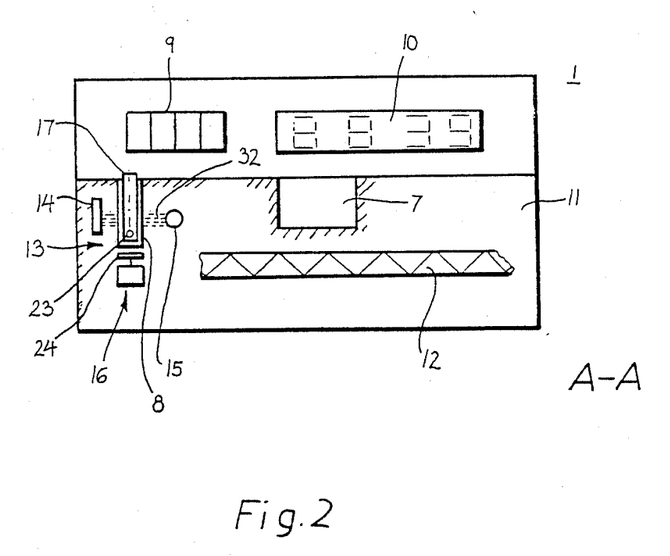
FIG. 2 the apparatus according to FIG. 1 in section A—A.
Figure 3:
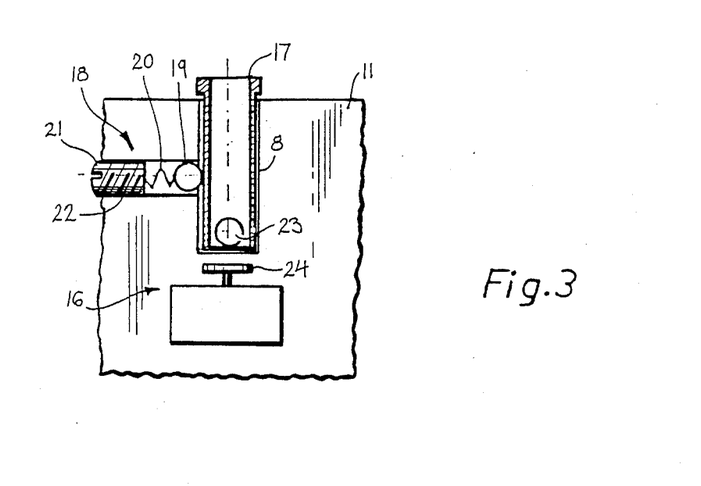
FIG. 3 the mounting support of the measuring cell as a larger-scale detail.

FIG. 2 shows that the metal unit 11 contains a heating system 12, which is preferably an electrical heating system. Heating system 12 uniformly heats measuring unit 11, so that the cells in preheaters 6, 7 (FIG. 1) and measuring channel 8 are uniformly heated. A light detector 14 and a light source 15 of a photooptical scanner 13 are provided on either side of measuring channel 8. Below the bottom of measuring channel 8 into which is introduced a measuring cell 17, a magnetic stirrer 16 is provided with a drive 24 producing in per se known manner a magnetic rotary field or provided with a horizontally rotating permanent magnet (FIGS. 2 and 3). On the bottom of measuring cell 17, there is a metal ball 23, which can be rotated by operative association with drive 24. Through the rotation of metal ball 23, the sample located in measuring cell 17 is thoroughly mixed.

A special clamping device 18 is provided for securing measuring cell 17 in measuring channel 8. The clamping device comprises a clamping member 19, which can for example have a spherical construction. Clamping member 19 is connected to a compression spring 20, which is connected to a setscrew 21. Setscrew 21 with compression spring 20 and clamping member 19 are screwed into a taphole 22 formed horizontally in measuring unit 11, whilst under the tension of compression spring 20, clamping member 19 engages with the wall of measuring cell 17. Thus, the latter is firmly held in measuring channel 8, without impairing the insertion and removal of cell 17 with respect to channel 8. Clamping device 18 is arranged in such a way that the photooptical path 32 (FIG. 4) of photooptical device 13 is not impaired.

Figure 4:
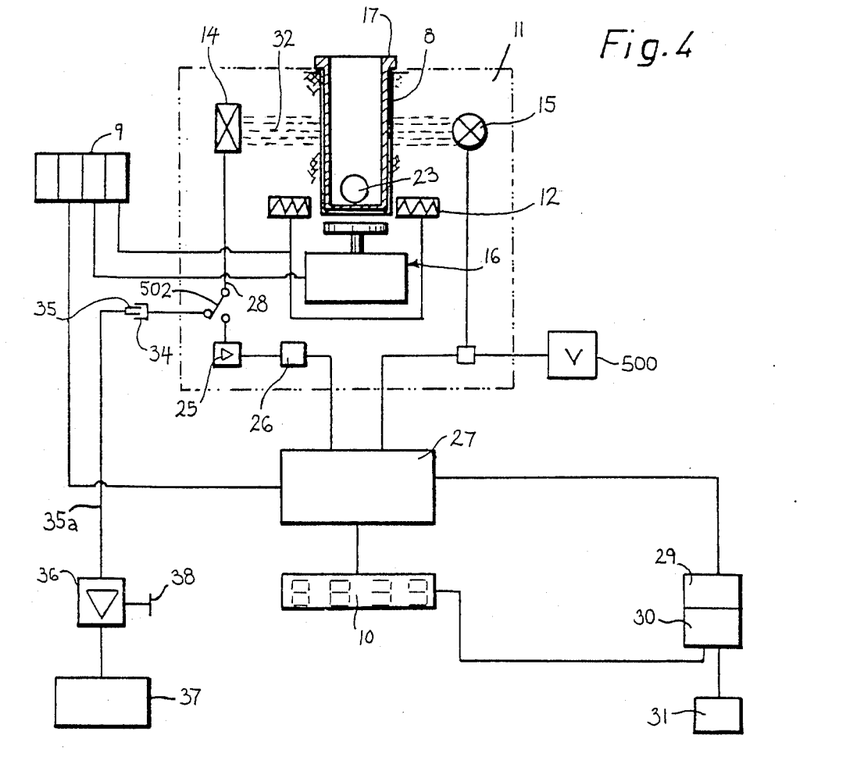
FIG. 4 the block diagram of a further apparatus according to the invention.

Light detector 14, constructed e.g. as a photoelectric cell, is connected via an amplifier 25 and a transmission adjuster 26 to the measured value unit 27, which is simultaneously operatively connected to light source 15. Measured value unit 27 controls the lamp voltage from source 500 and is adjustable via control panel 9 for adapting apparatus 1 to the particular sample to be measured. On the output side, measured value unit 27 is connected to display panel 10. Measured value unit 27 can also be connected to a computer and processing unit 29 which comprises a computer 30, connected on the output side with display panel 10 and optionally additionally to a printer 31. Computer 30 makes it possible, on the basis of the data determined by the measurement, to calculate the particular blood characteristics, store them and optionally mix and compare them with further diagnosis data.

The apparatus 1 can also be supplemented in such a way that it is possible to measure aggregation, so that on the basis of the measured values of the sample in measuring cell 17, conclusions can be drawn regarding a possible thrombosis risk. For this purpose, the light detector must be connected to an adjustable min/max amplifier 36, to whose output is connected a curve tracer 37. As shown in FIG. 4, it is possible to connect to the connecting line 28 between light detector 14 and amplifier 25, a socket 34, which can be located on the outer wall of casing 2. Plug 35 of a connecting cable 35a can be inserted in socket 34, said cable being connected to the min/max amplifier 36. A special setting member 38 is provided for the setting of the min/max amplifier 36. However, it is also possible to integrate the min/max amplifier 36 with the curve tracer 37 in apparatus 1. It is merely necessary for this purpose to provide in connecting line 28 a reversing switch 502, through the operation of which the light detector 14 is brought into operative connection with the min/max amplifier 36. In this operating state, the connection of amplifier 25 is blocked.

Due to the special magnetic mixing system realized in apparatus 1 and the controlled light path, an extremely reliable and precise determination of the blood clotting time is possible. The disadvantages present in other magnetic mixing systems are avoided through the use of a metal ball 23, which stresses the sample to be measured to such a minor extent, that there are no time lags in the turbidity process. As metal ball 23 cannot form a cavity in measuring cell 17, there can also be no air bubbles, with the resulting measuring errors. In addition, the metal ball 23 can be very easily separated, which greatly facilitates the use of the apparatus 1. Due to the controlled light path where the lamp voltage cannot drop below 50% of the rated voltage, the light source 15 emits so much light that the percentage extraneous light proportion is too low to lead to faults. In addition, the characteristic of the lamp voltage change is positioned in such a way that in the lower voltage range, i.e. approximately at 50% of the rated voltage, the amplification is greater than in the upper range, so that clear samples are much more reliably determined. As the linear range of the lamp voltage change to the light brightness and also the linear range of light detector 14 can be fully utilized, the range to be measured between clear and turbid samples is much greater than presently available. Through the use of a special measuring cell 17 with a band thickness e.g. reduced by 25%, it is also possible to carry out extreme measurements with dilute whole blood in apparatus 1. Cell 17 is preferably constructed in such a way that on adding 100 μl the photooptical path 32 is not affected, but on adding 200 μl is exceeded. Thus, constantly defined optical boundary conditions are present, which prevent self-starting of apparatus 1. Due to the appropriate construction of the opening part of measuring cell 17, it is ensured that extraneous light is not connected through the cell wall into the vicinity of the photooptical path 32. The two threshold value limiters provided in measuring value unit 27 permit immediate detection of clot formation with increasing transmission. An automatic transmission adjustment is brought about by the transmission adjuster 26. As a result, apparatus 1 can be used for all plasmas and reagents for all clotting determinations.

Figure 5:
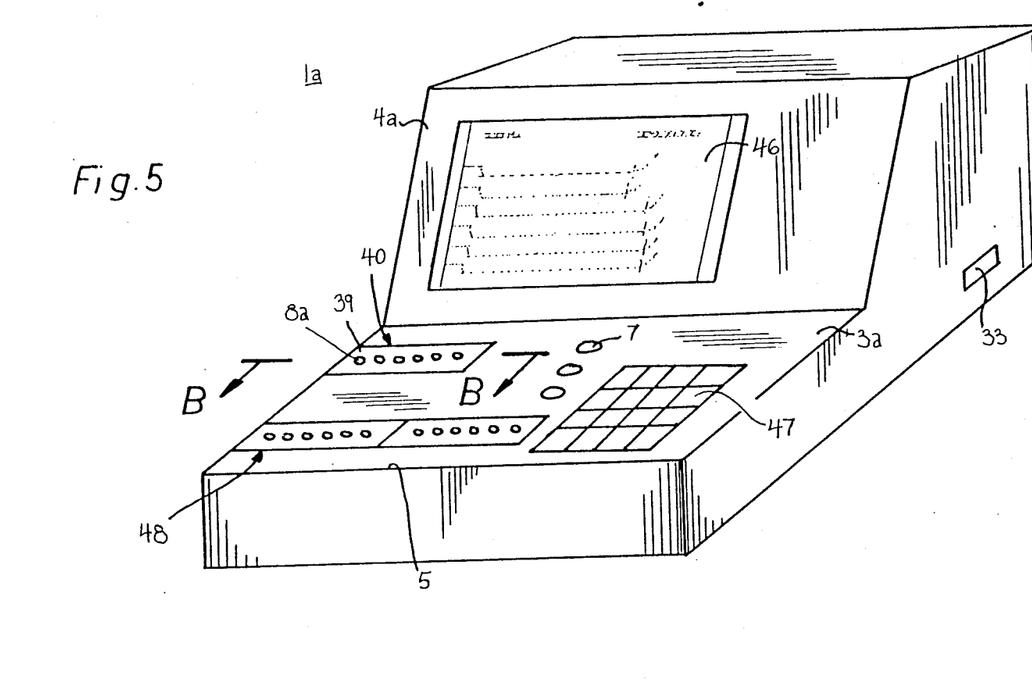
FIG. 5 a further embodiment of the apparatus according to the invention in a perspective view.

FIG. 5 shows an apparatus 1a, which is constructed as a multichannel clotting time measuring apparatus with a measured value display on a monitor 46. It also comprises a control part 3a and a measuring part 4a, monitor 46 being provided on the latter.

In each case, six measuring cells 17 can be mounted in the measuring channels 8a of a cell block or unit 39. One cell unit 39 can be inserted in a recess 40 of the temperature controllable measuring unit 11a in such a way that the cell 17 in channels 8a of unit 39 are in operative engagement with the magnetic stirrer 16a and the photooptical scanner 13a. Measuring surface 5 of measuring part 4 also contains recesses 48 serving as preheaters and is constructed for the preparatory securing of two cell units 39. In addition, three recesses serving as preheaters 7 are provided and receive reagent containers. Laterally of recesses 40, 48 and preheaters 7 is provided a button selector 47, used for operating apparatus 1a.

Figure 6:
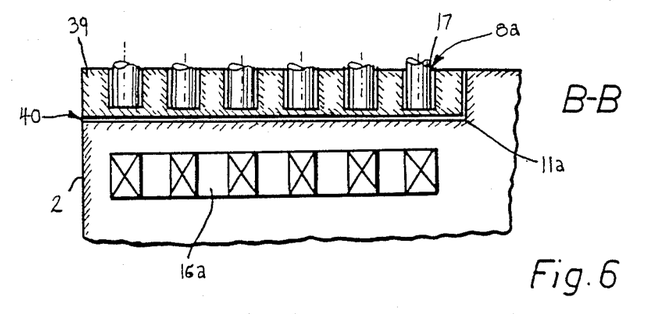
FIG. 6 a partial view of the apparatus in FIG. 5 in section B—B.
Figure 7A:
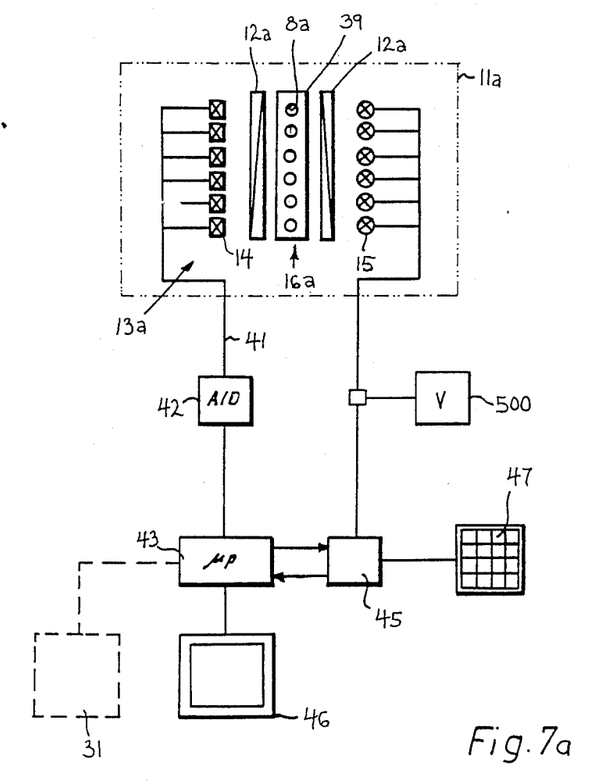
FIG. 7a a schematic block diagram of the apparatus of FIG. 5.

As is shown in FIG. 6, a cell unit 39 comprises a metal rail in which are arranged the measuring channels 8a. Cell unit 39 can be preheated to a temperature of 37° C., which is advantageous for incubation purposes. Magnetic stirrer 16a is arranged in recess 40 below measuring cell 39 and comprises a plurality of independently controllable stirring elements. Each stirring element is associated with a measuring channel 8a and consequently a measuring cell 17. As shown in FIG. 7a, this also applies to the scanning members of the photooptical scanner 13a. A light source 15 and a light detector 14 is associated with each cell 17 (FIG. 6) and they are in each case controllable separately from the other light sources 15 and light detectors 14. The light sources 15 are connected to votage source 500 which is controlled by control element 45. Two heating elements 12a serve to uniformly heat the cell unit 39.

Output line 41 connected to the light detectors 14 of the photooptical scanner 13a is connected to an analog-digital converter 42, connected to a microprocessor 43. Microprocessor 43 is connected across control element 45 to the button selector 47 and to a monitor 46 as the data output means. A printer 31 can also be connected to microprocessor 43, which can be programmed by the button selector 47. In accordance with its program, the microprocessor 43 selectively controls the photooptical scanning members of the photooptical scanner 13a associated with a measuring cell 17 in cell unit 39. Microprocessor 43 also controls the threshold value limiters.

Figure 7B:
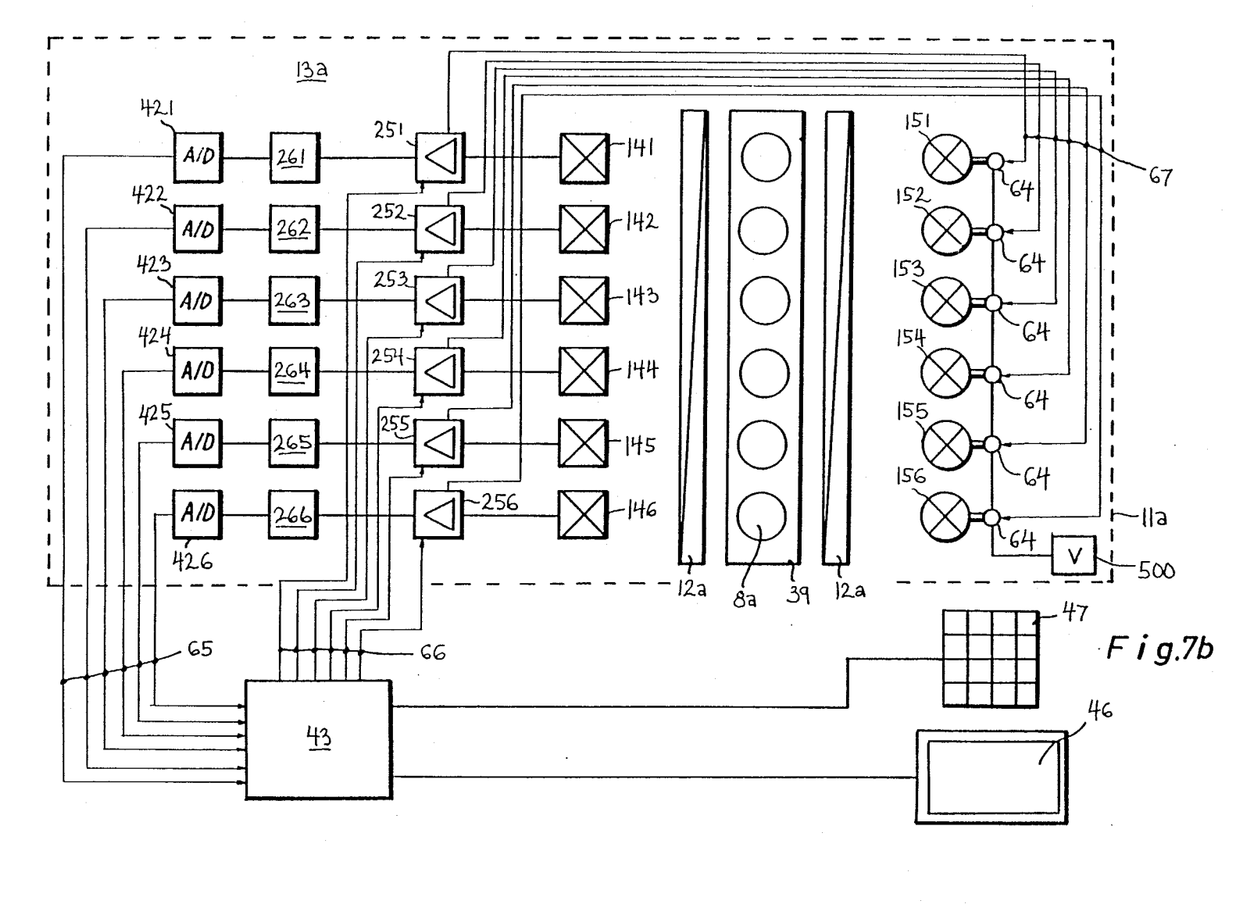
FIG. 7b a further schematic block diagram of the apparatus of FIG. 5.

FIG. 7b shows another embodiment of the apparatus 1a in the form of a block diagram. Each light detector 141 to 146 of light scanner 13a is connected across an amplifier 251 to 256 and a transmission adjuster 261 to 266 to an analogdigital converter 421 to 426. Each analog-digital converter 421 to 426 is connected to microprocessor 43. Thus, a data line 65 is provided between each analog-digital converter 421 to 426 and the microprocessor 43. Furthermore, each amplifier 251 to 256 is connected by means of a data line 66 to microprocessor 43 and by means of a control line 67 is in operative connection with the particular light source 151 to 156. Thus, control pulses of microprocessor 43 for setting the particular voltage circuit of the light scanner 13a are supplied across the corresponding amplifier 251 to 256 to light source 151 to 156. A control element 64, to which is connected a voltage source 500 and a control line 67, is associated with light source 151 to 156 for controlling the same. On constructing apparatus 1a in accordance with block diagram of FIG. 7b, the light scanning circuit associated with each measuring channel 8a can be individually controlled and regulated.

Figure 8:
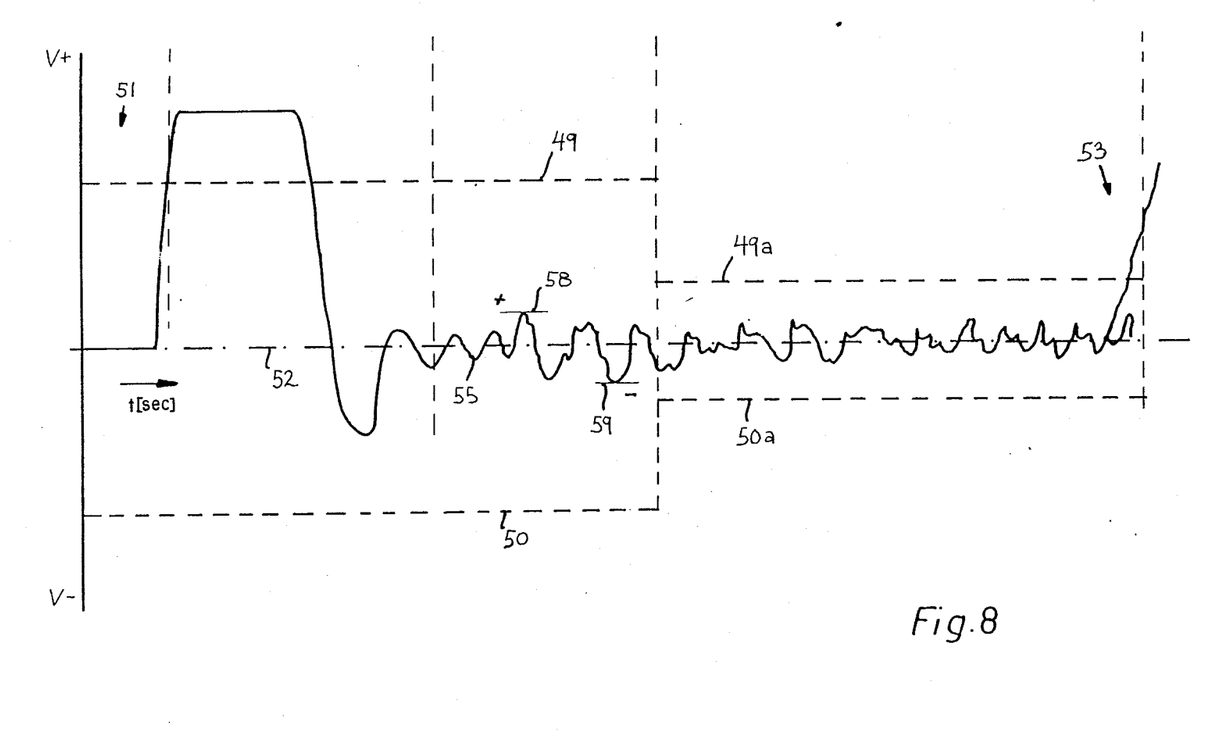
FIG. 8 a schematic measured value diagram.

The number of measuring channels 8a is dependent on the resolution of monitor 46, there can be e.g. six channels. The use of an apparatus 1a with monitor 46 with an analog data determination and a computer-controlled process sequence makes it possible for the microprocessor 43 to control the switching thresholds 49, 49a, 50, 50a (see FIG. 8) and to adapt to the instability of the particular measurement. In the initial position, the switching thresholds 49, 50 are so far apart that in each case a start is obtained by pipetting reagent into measuring cell 17. The large switching thresholds 49, 50 are intended to prevent faults, such as automatic starts. Following starting, the measuring signal 55 is automatically adjusted to the zero value 52. After adjustment, the maximum pulses 58, 59 of measured signal 55 are stored over a given time. At the end of the measuring time, the upper and lower adapted switching threshold 49a, 50a is positively and negatively drawn down over a given value of the maximum pulse 58, 59. As a result of this process sequence, the apparatus 1a is automatically optimized by means of microprocessor 43 with respect to all reagents and determinations (FIG. 8).

Figure 9:
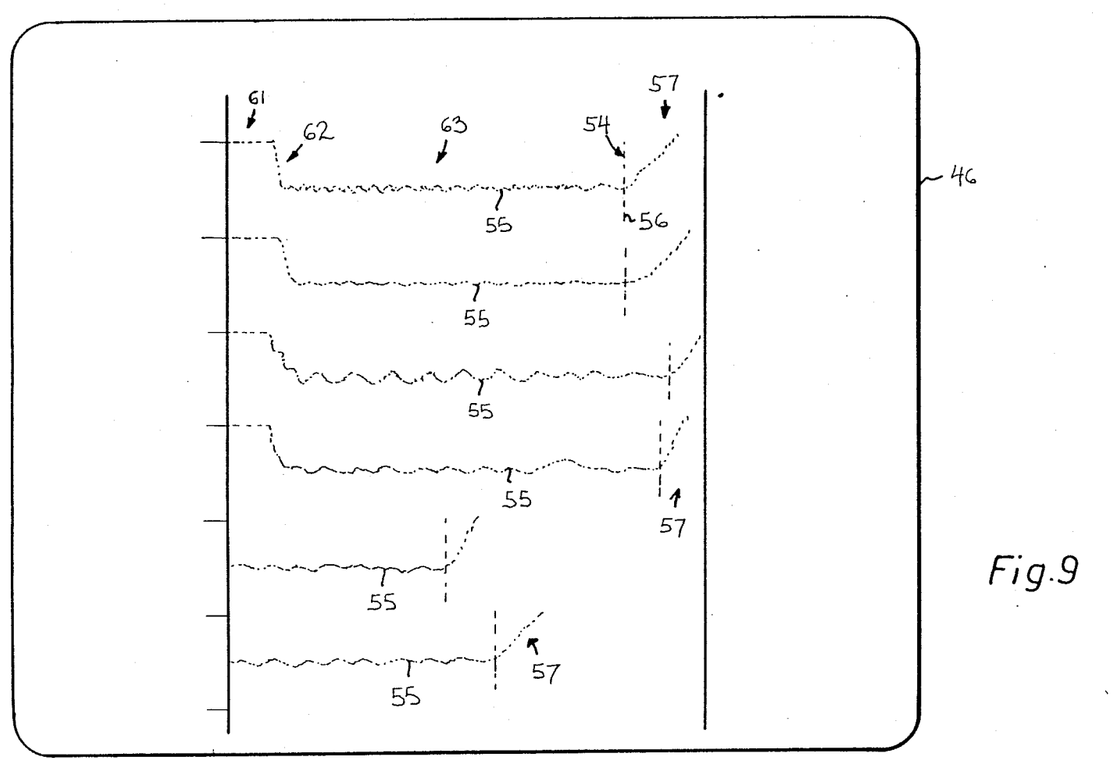
FIG. 9 a possible measured value display of the apparatus according to FIG. 1 in a diagrammatic view.

FIG. 9 shows an example of a display on a monitor 46. The dotted line curves show the phases start 61, zero balancing 62, switching threshold adaptation 63 and clot formation 54. Thus, monitor 46 provides information on all six coagulation sequences in measuring cells 17 in a simultaneous manner in the form of curves 55. The start of coagulation is represented in the form of a vertical dash 56 as the coagulation disconnection point and this passes through a curve 55. The continuation of coagulation or clotting is indicated by a follow-up control 57 of e.g. 3 seconds after the stop signal at the start of coagulation. Monitor 46 also gives information of the coagulation times in seconds, the percentage values calculated from the coagulation time, the means value in the case of a double determination, the determination taking place at the present time, the fed-in patient characteristics, the running sample number, the temperature of the measuring unit 11a, the incubation time and the set resolution of curves 55.

By means of the button selector 47, it is possible to feed in the patient characteristics, the disconnection point 53 (FIG. 8) of automatic coagulation detection can be displaced, the resolution of curves 55 can be selected, the printout via a printer 31 (FIG. 4) can be controlled, the particular determination can be fed in and the incubation can be started.

In addition, the scanning members of the photooptical scanner 13a and the stirring members of magnetic stirrer 16a associated with each individual measuring channel 8a can be started and stopped. By corresponding operation of the button selector 47, it is also possible to simultaneously reset all the measuring channels 8a. Thus, apparatus 1a makes it possible to carry out a plurality of blood clotting time measurements and is therefore particularly suitable for use wherever a large number of such measurements has to be carried out in a short time.

I claim:

1. Apparatus for measuring blood clotting time; said apparatus being suitable for use with a measuring cell having a bottom, the measuring cell containing a blood sample, the clotting time of which is to be measured; said apparatus comprising:
    temperature controlled support means having means defining at least one measuring channel, said measuring channel being capable of receiving the measuring cell containing the blood sample;
    magnetic stirring means mounted in said support means proximate to said means defining said measuring channel, said magnetic stirring means including a metal ball positionable at the bottom of the measuring cell when the cell is inserted in said channel, said magnetic stirring means further including a magnetic drive means proximate said means defining said measuring channel, said magnetic drive means being operable to rotate said ball in a circular path about the bottom of the measuring cell;
    photo optical turbidity detection means having a light source and a light detector forming a photo optical path containing the measuring cell when the cell is inserted in the channel, said light source being of a type such that, in lower portions of its operating voltage range, a given change in operating voltage results in a greater change in light output than in upper portions of its operating range, said light detector being connected through transmission signal adjustment means to a measured value means having two threshold value limiting means;
    voltage supply means for supplying an operating voltage to said light source which is at least half the rated voltage of said source;
    computer means coupled to said measured value means; and
    display means coupled to said measured value means for displaying visually perceptible information.

2. Apparatus according to claim 1 wherein said support means includes clamping means for retaining the measuring cell in said means defining said measuring channel.

3. Apparatus according to claim 2 wherein said clamping means includes a clamping member biased by spring mean for being pressed against the measuring cell when same is inserted in said means defining said measuring channel.

4. Apparatus according to claim 3 further including means for adjusting the bias applied to said clamping member by said spring means.

5. Apparatus according to claim 1 wherein said support means further includes means defining recesses serving as preheaters.

6. Apparatus according to claim 1 wherein said apparatus is further defined as apparatus for measuring aggregation in a blood sample and wherein said apparatus further includes an adjustable min/max amplifier having its input connected to said light detector and its output connected to a curve tracer, said apparatus including switch means for selectively connecting said light detector to said measured value means or said min/max amplifier.

7. Apparatus according to claim 6 wherein said support means includes a socket for a plug of a connecting cable of said min/max amplifier for connecting said light detector to said amplifier.

8. Apparatus for measuring blood blotting time, said apparatus being suitable for use with measuring cells; each of said measuring cells having a bottom and containing a blood sample, the clotting time of which is to be measured; said apparatus comprising:
    temperature controlled support means having means defining a recess for receiving block means defining a plurality of measuring channels, said measuring channels being capable of receiving the measuring cells containing the blood samples;
    magnetic stirring means mounted in said support means proximate to said block means, said magnetic stirring means including metal balls positionable at the bottom of the measuring cells when the cells are inserted in said channels, said magnetic stirring means further including magnetic drive means proximate said block means operable to rotate said balls in circular paths about the bottoms of the measuring cells;
    a plurality of photo optical turbidity detection means, each having a light source and a light detector forming a photo optical path containing a measuring cell when the cells are inserted in said channels, each of said light sources being of a type such that, in lower portions of its operating voltage range, a given change in operating voltage results in a greater change in light output than in upper portions of its operating range, said light detectors being connected to analog-digital converter means, microprocessor means coupled to said analog-digital converter means, said microprocessor being operable by control means and being connected to a data output device for displaying visually perceptible information; and
    voltage supply means for supplying an operating voltage to said light sources which is at least half the rated voltage of said sources.

9. Apparatus according to claim 8 wherein said data output device comprises at least one of a printer or a monitor.

10. Apparatus according to claim 8 wherein said control means comprises a touch pad for programming said microprocessor.

11. Apparatus according to claim 8 wherein said support means includes means defining additional recesses for receiving and preheating said block means.

12. Apparatus for measuring blood clotting time, said apparatus being suitable for use with measuring cells; each of said measuring cells having a bottom and containing a blood sample, the clotting time of which is to be measured; said apparatus comprising:

temperature controlled support means having means defining a recess for receiving block means defining a plurality of measuring channels, said measuring channels being capable of receiving the measuring cells containing the blood samples;

magnetic stirring means mounted in said support means proximate to said block means, said magnetic stirring means including metal balls positionable at the bottom of the measuring cells when the cells are inserted in said channels, said magnetic stirring means further including magnetic drive means proximate said block means and being operable to rotate said balls in circular paths about the bottoms of the measuring cells;

a plurality of photo optical turbidity detection means, each having a light source and a light detector forming a photo optical path containing a measuring cell when the cells are inserted in said channels, each of said light sources being of a type such that, in lower portions of its operating voltage range, a given change in operating voltage results in a greater change in light output than in upper portions of its operating range, each of said light detectors being connected through a series connected amplifier, transmission signal adjuster, and analog-digital converter means to a microprocessor, said microprocessor being operable by control means and being connected to a data output device or displaying visually perceptible information, each of said amplifiers being connected to the light source associated with the corresponding light detector and to said microprocessor, whereby said microprocessor selectively controls and operates said light sources and light detectors; and voltage supply means for supplying an operating voltage to said light sources which is at least half the rated voltage of said sources.

* * * * *